United States Patent [19]

Blank et al.

[11] Patent Number: 5,030,747

[45] Date of Patent: Jul. 9, 1991

[54] PROCESS FOR THE PREPARATION OF μ-AMINO-ACRYLIC ACID ESTERS

[75] Inventors: Heinz U. Blank, Odenthal; Erich Wolters, Cologne; Friedrich-Wilhelm Ullrich, Cologne; Halmut Kraus, Cologne; Gerhard Marzolph, Cologne; Gunter Silber, Cologne, all of Fed. Rep. of Germany

[73] Assignee: Bayer Aktiengesellschaft, Leverkusen, Fed. Rep. of Germany

[21] Appl. No.: 495,522

[22] Filed: Mar. 19, 1990

[30] Foreign Application Priority Data

Mar. 23, 1989 [DE] Fed. Rep. of Germany ....... 3909596
Mar. 23, 1989 [DE] Fed. Rep. of Germany ....... 3909598

[51] Int. Cl.$^5$ ............................................. C07C 227/08
[52] U.S. Cl. ...................................... 560/172; 560/43
[58] Field of Search ............................ 560/172, 38, 43

[56] References Cited

U.S. PATENT DOCUMENTS

| | | | |
|---|---|---|---|
| 2,987,491 | 6/1961 | Bader et al. | 560/172 |
| 4,027,037 | 5/1977 | Siegle et al. | 560/172 |
| 4,046,803 | 9/1977 | Heckles | 560/172 |
| 4,723,031 | 2/1988 | Lo | 560/172 |
| 4,772,711 | 9/1988 | Englaender et al. | 560/172 |

FOREIGN PATENT DOCUMENTS 0728187 2/1966 Canada ............................... 569/172

*Primary Examiner*—James H. Reamer

*Attorney, Agent, or Firm*—Sprung Horn Kramer & Woods

[57] ABSTRACT

β-Amino-acrylic acid esters of the formula $$(R^1R^2)NCH=CR^3-COOR^4$$

can be obtained by reaction of β-hydroxy-acrylic acid ester alkali metal salts of the formula $$Me^\oplus \ ^\ominus OCH=CR^3-COOR^4$$

with ammonium salts of the formula $$(R^1R^2)NH_2^\oplus \ ^\ominus$$

according to the general reaction equation $$(R^1R^2)NH_2X + MeOCH=CR^3-COOR^4 \rightarrow (R^1R^2)NCH=CR^3-COOR^4 + MeX = H_2O$$

$R^1$, $R^2$, $R^3$, $R^4$, $Me^\oplus$ and $X^\ominus$ having the meaning indicated in the description and the reaction being carried out in an aprotic organic solvent, in which the reaction components are suspended, as the reaction medium and it being possible to replace a part of the aprotic organic solvent by a protic organic solvent which is miscible with the aprotic solvent to give a homogeneous phase.

20 Claims, No Drawings

PROCESS FOR THE PREPARATION OF β-AMINO-ACRYLIC ACID ESTERS

BACKGROUND OF THE INVENTION

The present invention relates to a process for the preparation of β-amino-acrylic acid esters from β-hydroxy-acrylic acid ester alkali metal salts and ammonium salts in an aprotic organic solvent. The reaction is in this case accomplished according to the general reaction equation:

$$(R^1R^2)NH_2X + MeOCH=CR^3-COOR^4 \rightarrow (R^1R^2)NCH=CR^3-COOR^4 + MeX + H_2O$$

β-Amino-acrylic acid esters are employed in the synthesis of pharmaceutically active 4-hydroxy-quinoline derivatives.

SUMMARY OF THE INVENTION

A process for the preparation of β-amino-acrylic acid esters of the formula $$(R^1R^2)NCH=CR^3-COOR^4 \quad (I)$$

by reaction of β-hydroxy-acrylic acid ester alkali metal salts of the formula $$Me^{\oplus\ominus}OCH=CR^3-COOR^4 \quad (II)$$

with ammonium salts of the general formula $$(R^1R^2)NH_2^{\oplus}X^{\ominus} \quad (III)$$

in which $R^1$, $R^2$ and $R^3$ independently of one another denote hydrogen, straight-chain or branched $C_1$-$C_8$-alkyl, straight-chain or branched $C_2$-$C_8$-alkenyl, $C_3$-$C_8$-cycloalkyl, $C_5$-$C_{12}$-aryl or a 5-7-membered aromatic or non-aromatic heterocyclic system having 1 or 2 heteroatoms from the group comprising N and/or S and/or O, $R^1$ and $R^2$, together with the N atom substituted by them, can form an aromatic or non-aromatic heterocyclic system which, in addition to the N atom, can contain a further heteroatom from the group comprising N and/or S and/or O, $R^4$ represents straight-chain or branched $C_1$-$C_8$-alkyl, $Me^{\oplus}$ represents an alkali metal ion and $X^{\ominus}$ denotes the anion of an inorganic or organic acid, has been found, which is characterized in that the reaction is carried out in an aprotic organic solvent, in which the reaction components are suspended, as the reaction medium, it being possible to replace a part of the aprotic solvent by a protic organic solvent which is miscible with the aprotic solvent to give a homogeneous phase.

DETAILED DESCRIPTION OF THE INVENTION

Straight-chain or branched $C_1$-$C_8$-alkyl is, for example, methyl, ethyl, propyl, isopropyl, butyl, isobutyl, tert.-butyl, or the isomeric pentyls, hexyls or octyls. The said $C_1$-$C_4$-alkyl radicals, particularly preferably methyl or ethyl and very particularly preferably methyl, may be mentioned in preference.

Straight-chain or branched $C_2$-$C_8$-alkenyl is vinyl, propenyl, allyl, 1-butenyl, 2-butenyl, or the isomeric pentenyls, hexenyls and octenyls. $C_2$-$C_4$-Alkenyl may be preferably mentioned.

$C_3$-$C_8$-Cycloalkyl is, for example, cyclopropyl, cyclobutyl, cyclopentyl, methyl-cyclopentyl, dimethyl-cyclopentyl, cyclohexyl, methyl-cyclohexyl, dimethyl-cyclohexyl, cycloheptyl and cyclooctyl. Preferred cycloalkyl is cyclopropyl, cyclopentyl and cyclohexyl.

$C_6$-$C_{12}$-Aryl is, for example, phenyl, naphthyl or biphenylyl, preferably phenyl.

As the 5-7 membered, aromatic or non-aromatic heterocyclic system having 1 or 2 heteroatoms from the group comprising N and/or S and/or O may be mentioned, for example: the radicals linked in the 2-, 3- or 4-position of pyrrole, pyrroline, pyrrolidine, furan, tetrahydrofuran, thiophene, tetrahydrothiophene, pyrazole, imidazole, pyrazoline, imidazoline, oxazole, thiazole, oxazoline, thiazoline, pyridine, pyran, thiopyran, piperidine, pyridazine, pyrimidine, pyrazine, oxazine, thiazine, azepine, oxazepine, thiazepine and thiazocine. 5- or 6-membered aromatic or non-aromatic heterocyclic systems of the type mentioned may be understood in preference, in which at least one of the heteroatoms is N.

The radicals mentioned may in turn be substituted by $C_1$-$C_4$-alkyl, preferably methyl, by $C_1$-$C_4$-alkoxy, preferably methoxy, by halogen, such as chlorine, fluorine or bromine, or by phenyl or hydroxyl. The series of aralkyl radicals is obtained, for example, by the phenyl substitution of alkyl. The aromatic moieties of the radicals and substituents mentioned may furthermore be substituted by typically aromatic substituents, such as nitro or cyano. The heterocyclic radicals may be fused to a benzene nucleus.

$R^1$ and $R^2$ may preferably be straight-chain or branched $C_1$-$C_4$-alkyl, particularly preferably $C_1$-$C_2$-alkyl and very particularly preferably methyl. $R^3$ may preferably be hydrogen or straight-chain or branched $C_1$-$C_4$-alkyl, particularly preferably hydrogen. $R^4$ may preferably be straight-chain or branched $C_1$-$C_4$-alkyl, particularly preferably methyl or ethyl.

$Me^{\oplus}$ is an alkali metal ion, for example the cation of Li, Na, K, Rb or Cs, preferably of Na or K, particularly preferably of Na.

$X^{\ominus}$ is the anion of an inorganic or organic acid. Possible inorganic acids are, for example, HF, HCl, HBr, $H_2SO_4$, $HNO_3$, $H_3PO_4$, and organic acids are one of the lower carboxylic acids, such as formic acid, acetic acid, propionic acid or butyric acid, furthermore halogenated lower carboxylic acids, such as chloroacetic acid, dichloroacetic acid, trichloroacetic acid, trifluoroacetic acid and the like, and also a sulphonic acid, such as methanesulphonic acid, benzenesulphonic acid or toluenesulphonic acid. One of the said inorganic acids may be mentioned as, particularly preferably HCl, preferred.

The β-hydroxy-acrylic acid ester alkali metal salts with the trivial name "($R^3$-substituted) formylacetic acid ester alkali metal salts" to be reacted according to the invention can be prepared, for example, by the action of CO on alkali metal alkoxide and ($R^3$-substituted) alkyl acetate.

The preparation of ethyl N,N-dimethyl-β-amino-acrylate from sodium ethyl formylacetate and dimethylamine hydrochloride is known from Annales de Chimie, 10th series, Vol. 18 (1932) 107 and, particularly, 108. In this preparation, a yield of 41% of the theoretical yield is achieved in absolute ethanol in a 7-8 hours' reaction.

The isolation of the desired product is difficult and entails heavy losses.

In the process described in DE-OS (German Published Specification) 3,531,067 to give the same final product, as described above, the yield is increased to approximately 75% of the theoretical yield by carrying out the reaction in an aqueous solution of the dialkylamine hydrochloride; the reaction time can in this case be reduced to approximately 2 hours. However, even in this process it is difficult to isolate the β-amino-acrylic acid ester from the reaction mixture without relatively large losses. This applies in particular to compounds with small alkyl radicals, which are relatively easily water-soluble and are retained in the reaction medium in a relatively large amount such as occurs, for example, with methyl N,N-dimethyl-β-amino-acrylate. The process described in DE-OS (German Published Specification) '067 has the further disadvantage that water is a reaction medium in which the starting compounds are rapidly decomposed, very particularly under slightly acidic conditions, so that the contact of the alkali metal hydroxy-acrylic acid ester with the water should be kept to a minimum. The result is that the scope of the process is greatly restricted, which in many cases makes a more complicated procedure necessary. The manner of addition is thus fixed, and it is not possible according to this DE-OS, for example, to combine the reaction to give the β-amino-acrylic acid ester with the preliminary step to give a one-pot reaction in which the alkali metal hydroxy-acrylic acid ester is reacted further to the β-amino-acrylic acid ester by addition of dimethylamine hydrochloride without intermediate isolation, since in this case losses in yield cannot be avoided according to the process of DE-OS (German Published Specification) '067. This last-mentioned manner of addition by combining two steps to give a one-pot reaction is therefore also indicated as negative in this DE-OS.

According to the invention, the β-amino-acrylic acid esters (I) can be obtained according to the above general equation in high purity, in nearly quantitative yields and with short reaction times by carrying out the reaction in an aprotic organic solvent, in which the reaction components are suspended, as the reaction medium, it being possible to replace a part of the aprotic organic solvent by a protic organic solvent which is miscible with the aprotic solvent to give a homogeneous phase. A wide scope for the process and simple isolation are possible. The yields of β-amino-acrylic acid esters, relative to the β-hydroxy-acrylic acid ester alkali metal salt employed, are thus as a rule above 90% of the theoretical yield of at least 99% pure reaction product.

Suitable aprotic organic solvents are, for example, benzene derivatives, aliphatic hydrocarbons, esters, nitriles, amides and ethers or mixtures thereof.

Possible benzene derivatives are, for example, benzene itself, furthermore benzenes substituted by 1 to 3 $C_1$-$C_4$-alkyl groups and/or 1 to 3 alkoxy groups and/or 1 to 2 halogen atoms, such as chlorine or bromine; the substituted benzenes are in particular those whose substituents include 1 to 6 additional atoms. Examples of these are: benzene, toluene, xylenes, cumene, ethylbenzene, chlorobenzene, chlorotoluene, dichlorobenzene etc.

As reaction media, aliphatic hydrocarbons may be straight-chain or branched and contain 5–10 C atoms and are present in pure form or as a mixture. Examples are, for example, petroleum ether and ligroin.

Esters are, for example, ethyl acetate, methyl propionate etc.; nitriles are, for example, acetonitrile, benzonitrile etc.; amides are, for example, dimethylformamide, dimethylacetamide etc.

Suitable ethers may be open-chain or cyclic compounds having 4–8 C atoms, such as tetrahydrofuran, dioxane, dibutyl ether, methyl tert.-butyl ether and the like.

For a simple distillative isolation, the boiling point of the chosen solvent should either be clearly above or below the boiling point of the desired compound.

In preference, toluene, xylene, ethyl acetate or a mixture of two or all of these substances are employed as aprotic solvents.

Suitable protic organic solvents are: $C_1$-$C_8$-alkanols, phenol or phenol substituted by methyl groups, ethyl groups, chlorine and/or bromine, or mixtures thereof. Such protic solvents have a $pK_a$ value which is greater than 10. An alkanol, particularly preferably a $C_1$-$C_4$-alkanol, and very particular preferably methanol and/or ethanol is employed in preference.

The ratio of the aprotic to the protic solvent is 1:10–10:1 parts by weight, preferably 1:2–7:1 parts by weight.

The amount of the aprotic organic solvent or of a mixture of aprotic and protic solvents employed has only to be chosen such that at any time a good mixing of the suspension is ensured using the stirrer present in the reaction apparatus and the resultant reaction product at the end of the reaction is as far as possible completely present in this solvent in dissolved form. For this purpose, for example, an amount of 130% by weight to 500% by weight of solvent (mixture), relative to β-hydroxy-acrylic acid ester alkali metal salt employed, may be mentioned.

The reaction components (II) and (III) may be employed in stoichiometric amounts. However, an excess of the cheaper component (in general the ammonium salt) of 1–80 mol-%, relative to the more expensive component, is advantageously employed. In preference, therefore, an excess of ammonium salt, for example of 7–30 mol-%, is usually employed. The molar ratio of β-hydroxy-acrylic acid ester alkali metal salt to ammonium salt is therefore 1:0.7–1.8, preferably 1:1.07–1.3.

In the process according to the invention, the reaction proceeds sufficiently rapidly even at low temperatures of 0° C. and lower. At temperatures above 60° C., the formation of by-products distinctly increases. Convenient reaction temperatures are therefore 0°–60° C., preferably 15° to 30° C.

The number and spread of the possible procedures is large because of the essentially lower instability of the β-hydroxy-acrylic acid ester alkali metal salts in the aprotic or aprotic/protic reaction medium.

For example, the reaction can be carried out by adding the β-hydroxy-acrylic acid ester alkali metal salt in solid form or as a suspension in a solvent according to the invention to the suspension or solution of the ammonium salt in a solvent according to the invention with good stirring. If the reaction is carried out in a mixture of aprotic and protic solvents, the ammonium salt is advantageously present as a suspension in a protic solvent.

Another procedure consists in adding the ammonium salt in solid form or as a suspension in a solvent according to the invention to the suspension of the β-hydroxy-acrylic acid ester alkali metal salt in a solvent according to the invention with good stirring.

A still further process variant consists in adding the respective amine, in concentrated form or diluted with one of the aprotic or protic organic solvents mentioned to the suspension of the β-hydroxy-acrylic acid ester alkali metal salt in a solvent according to the invention and then adding an amount of an inorganic or organic acid, for example hydrogen chloride, corresponding to the β-hydroxy-acrylic acid ester alkali metal salt with good stirring. The addition of amine and acid can also be carried out simultaneously with control of their equivalent proportions (for example with a pH electrode).

In a preferred embodiment, the β-hydroxy-acrylic acid ester alkali metal salt is obtained by its prepration by means of reaction of the corresponding carboxylic acid ester with CO and alkali metal alkoxide in a reaction medium of aprotic organic solvent according to the invention and is in general present as a suspension. The ammonium salt in solid form and, if appropriate, additional protic solvent or, particularly preferably, as a suspension in an aprotic and/or protic solvent or, as already described above, first as the pure amine (if appropriate diluted with one of the solvents mentioned) and subsequent addition of the acid, is now added to this suspension of the alkali metal salt with good stirring.

In another preferred embodiment, the suspension obtained from the preliminary step is added in an aprotic solvent to a suspension of the ammonium salt in an aprotic and/or protic solvent. The β-amino-acrylic acid esters can be prepared by such a procedure in a one-pot reaction with total yields of 80-95%, relative to the carboxylic acid ester employed or relative to the alkali metal alkoxide employed.

In contrast to the known processes, the separation of the reaction product is simple and takes place, to judge from the yield, virtually quantitatively. After the water of reaction has been removed azeotropically by incipient distillation, whereupon protic solvents which may additionally be used partially pass over, the alkali metal salt of the inorganic or organic acid formed can be easily filtered off. The retention of reaction product in solvents to be separated off observed in the known processes does not occur in the process according to the invention. The organic solvents to be employed according to the invention prove to be inert with respect to the reaction product in the distillative work-up following the salt separation. Thus, hardly any residue, which could indicate considerable amounts of by-products, typically remains after the distillative removal of the solvent and the likewise distillative recovery of the reaction product. A very pure product of more than 98%, frequently more than 99%, purity is thus obtained without further precision distillation.

EXAMPLE 1

Methyl β-(N,N-dimethylamino)-acrylate 27.5 g (0.61 mol) of condensed dimethylamine were added dropwise at 0° to 5° C. to 120 ml of toluene. 21.9 g (0.60 mol) of hydrogen chloride were then introduced at the same temperature with cooling. 74.4 g of 90.0% pure sodium methyl formylacetate (0.54 mol) were then introduced with good stirring as the solid in the course of a half hour while warming to 20° to 25° C. The weakly exothermic reaction was kept to a temperature of approximately 25° C. by cooling slightly with an icebath and the mixture was subsequently stirred for one hour. The initially thick suspension became increasingly mobile during the addition of the first half of the sodium formylacetic acid ester and its colour changed from beige to yellowish orange. Low-boiling components and about 80 to 90% of the toluene were removed by distillation at a slight vacuum (about 300 mbar) in the rotary evaporator. The water of reaction was also removed from the mixture azeotropically in the course of this. The sodium chloride and the excess of dimethylammonium chloride formed were filtered off with suction and washed with 50 ml of toluene. The combined filtrates were distilled in vacuo without a column. After a forerun of residual toluene, 69.0 g of methyl N,N-dimethyl-β-aminoacrylate passed over at 1.0 mbar and a head temperature of 65° to 70° C.

A residue of 1.5 g, which for the largest part consisted of further product, remained in the distillation flask.

The product is slightly yellow-coloured and crystallizes after standing briefly in the distillation receiver. Melting point: 48°-50° C.

The purity determined by gas chromatography was 99.6% by weight.

This corresponded to a yeild of 98.6% of the theoretical yeild, relative to the sodium methyl formylacetate employed.

EXAMPLE 2

Ethyl β-(N,N-dimethylamino)-acrylate 120 ml of a toluene suspension of 50.40 g (0.62 mol) of dimethylammonium chloride were introduced with good stirring in the course of half an hour into 274.5 g of a toluene suspension which originated from the preparation of sodium ethyl formylacetate and which contained 71.2 g (0.515 mol) of sodium ethyl formylacetate. The reddish orange-coloured, mobile suspension was freed on a rotary evaporator in a slight vacuum (about 300 mbar) from low-boiling components and from about 80 to 90% of the toluene including the water passing over azeotropically. The solids were filtered off with suction and washed with 50 ml of toluene, and the combined filtrates were distilled in vacuo without a column. After a forerun of toluene, 85.8 g of colourless ethyl N,N-dimethyl-β-aminoacrylate passed over at 0.6 mbar and a head temperature of 94° to 95° C.

A residue of 2.7 g, which for the largest part consisted of further product, remained in the distillation flask.

The purity determined by gas chromatography was 99.8% by weight.

This corresponded to a yield of 96.8% of the theoretical yeild, relative to sodium ethyl formylacetate employed.

EXAMPLE 3

Ethyl β-(N,N-dimethylamino)-acrylate

A suspension of 34.0 g (0.5 mol) of sodium ethoxide in 200 ml of toluene and 66.1 g (0.75 mol) of ethyl acetate was initially introduced into a 0.7 liter autoclave. After flushing with nitrogen and then with carbon monoxide, a CO pressure of 20 bar was set by means of the reducing valve and the mixture was heated to 60° C.

Temperature and pressure were kept constant. The uptake of CO was complete after 5 hours.

After cooling to room temperature, the thick, beige-coloured suspension was added dropwise at room temperature with good stirring in the course of half an hour to an initially introduced suspension of 40.8 g (0.5 mol) of dimethylammonium chloride in 100 ml of toluene.

The temperature was kept to approximately 25° C. by cooling slightly with an icebath and the mixture was subsequently stirred for one hour.

After the sodium chloride and the excess of dimethylammonium chloride formed had been filtered off with suction and washed with 50 ml of toluene, the combined filtrates were distilled in vacuo without a column.

After a forerun of toluene, 65.7 g of colourless ethyl β-(N,N-dimethylamino)-acrylate passed over at 0.6 mbar and a head temperature of 88° to 96° C. A residue of 2.1 g remained in the distillation flask.

The purity determined by gas chromatography was 98.9% by weight. This corresponds to a yield of 90.8% of theory, relative to sodium ethoxide employed.

EXAMPLE 4

The suspension of 68 g (1 mol) of 93 percent sodium ethoxide in 132 g (1.5 mol) of ethyl acetate and 300 ml of toluene was initially introduced into a 1 liter autoclave. After heating to 50° C., a CO pressure of 20 bar was set. 4 h later, the CO uptake was complete and the autoclave was allowed to cool.

The contents of the autoclave were then added dropwise at room temperature to a suspension of 81.6 g (1 mol) of dimethylamine hydrochloride in 70 ml of methanol. After stirring for 2 h, the precipitate was filtered off with suction and washed with 30 ml of toluene, and the filtrate was concentrated on a rotary evaporator. During the subsequent vacuum distillation at 0.7 mbar and 83°–89° C., 123.5 g of 98.6% pure ethyl β-(N,N-dimethylamino)-acrylate were obtained, which corresponds to a yield of 94.2% over both steps. The residue consisted of 3.3 g of brown-coloured salt.

EXAMPLE 5

A suspension of 54 g (1 mol) of 91.5 percent sodium methoxide in 111 g (1.5 mol) of methyl acetate and 250 ml of toluene was heated to 80° C. and a CO pressure of 40 bar was set. After the CO uptake was complete (4 h), the mixture was allowed to cool and the resulting suspension was added dropwise to 81.6 g (1 mol) of dimethylamine hydrochloride in 100 ml of methanol. After stirring for 2 h, the mixture was concentrated to one half. The salt was filtered and washed with 30 ml of toluene, and the solvent was removed from the filtrate by distillation. Subsequent vacuum distillation yeilded 105.5 g of 99.6 percent product, which corresponds to a yield of 89% over both steps.

EXAMPLE 6

24 g (0.29 mol) of dimethylamine hydrochloride were initially introduced into a mixture of 50 ml of toluene and 50 ml of ethanol. 40 g (0.29 mol) of 92.6 percent sodium ethyl formylacetate were added with the aid of a metering device for solids in the course of 10 minutes. After stirring at 20° C. for 2 h, the precipitate was filtered off with suction. Working up yielded 35.0 g of 98.4 percent product, which corresponds to a yield of

EXAMPLE 7

The mixture from Example 6 was carried out in a solvent mixture of 54 ml of toluene, 36 ml of ethanol and 16 ml of ethyl acetate. A yield of 88.7% was obtained.

EXAMPLE 8

13.1 g (0.29 mol) of dimethylamine were introduced into a suspension of 40 g (0.29 mol) of sodium ethyl formylacetate in 50 ml of toluene and 50 ml of ethanol. HCl gas was then introduced until the point of neutrality was reached and the mixture was stirred at 20° C. for 2 h. After filtering off the precipitate with suction, the mixture was worked up in a customary manner. Ethyl β-dimethylaminoacrylate was obtained in a yield of 91.6%.

What is claimed is:

1. A process for the preparation of β-amino-acrylic acid esters of the formula $$(R^1R^2)NCH=CR^3-COOR^4$$

by reaction of β-hydroxy-acrylic acid ester alkali metal salts of the formula $$Me^{\oplus \ominus}OCH=CR^3-COOR^4$$

with ammonium salts of the general formula $$(R^1R^2)NH_2^{\oplus}X^{\ominus},$$

in which
  $R^1$, $R^2$ and $R^3$ independently of one another denote hydrogen, straight-chain or branched $C_1$–$C_8$-alkyl, straight-chain of branched $C_2$–$C_8$-alkenyl, $C_3$–$C_8$-cycloalkyl, $C_6$–$C_{12}$-aryl or a 5–7-membered aromatic or non-aromatic heterocyclic system having 1 or 2 heteroatoms from the group comprising N and/or S and/or O,
  $R^1$ and $R^2$, together with the N atom substituted by them, can form an aromatic or non-aromatic heterocyclic system which, in addition to the N atom, can contain a further heteroatom from the group comprising N and/or S and/or O,
  $R^4$ represents straight-chain or branched $C_1$–$C_8$-alkyl,
  $Me^{\oplus}$ represents an alkali metal ion and
  $X^{\ominus}$ denotes the anion of an inorganic or organic acid, wherein the reaction is carried out in an aprotic organic solvent, in which the reaction components are suspended, as the reaction medium, it being possible to replace a part of the aprotic solvent by a protic organic solvent which is miscible with the aprotic solvent to give a homogeneous phase.

2. The process of claim 1, wherein $R^1$ and $R^2$ represent straight-chain or branched $C_1$–$C_4$-alkyl.

3. The process of claim 2, wherein $R^1$ and $R^2$ represent $C_1$–$C_2$-alkyl.

4. The process of claim 3, wherein $R^1$ and $R^2$ represent methyl.

5. The process of claim 1, wherein $R^3$ represents hydrogen or straight-chain or branched $C_1$–$C_4$-alkyl.

6. The process of claim 5, wherein $R^3$ represents hydrogen.

7. The process of claim 1, wherein $R^4$ denotes straight-chain or branched $C_1$–$C_4$-alkyl.

8. The process of claim 6, wherein $R^4$ denotes methyl or ethyl.

9. The process of claim 1, wherein $Me^{\oplus}$ represents $Na^{\oplus}$ or $K^{\oplus}$, and $X^{\ominus}$ is the anion of an inorganic acid.

10. The process of claim 9, wherein $Me^{\oplus}$ represents $Na^{\oplus}$.

11. The process of claim 9, wherein $X^{\ominus}$ is the chloride anion.

12. The process of claim 1, wherein toluene, xylene, ethyl acetate or a mixture of two or all of these substances is employed as the aprotic solvent and a straight-chain or branched $C_1$–$C_4$-alcohol is employed as the protic solvent.

13. The process of claim 12, wherein methanol or ethanol is employed as the protic solvent.

14. The process of claim 1, wherein the molar ratio of $\beta$-hydroxy-acrylic acid ester alkali metal salt to ammonium salt is 1:0.7–1.8.

15. The process of claim 14, wherein the molar ratio of $\beta$-hydroxy-acrylic acid ester alkali metal salt to ammonium salt is 1:1.01–1.8.

16. The process of claim 15, wherein the molar ratio of $\beta$-hydroxy-acrylic acid ester alkali metal salt to ammonium salt is 1:1.07–1.3.

17. The process of claim 1, wherein as the $\beta$-hydroxy-acrylic acid ester alkali metal salt, the suspension present from its preparation from carboxylic acid ester, alkali metal alkoxide and CO in an aprotic organic solvent is employed, to which the ammonium salt is added in solid form.

18. The process of claim 17, wherein as the ammonium salt, the suspension in an aprotic or protic organic solvent or a mixture of such solvents is employed, or separately initially as pure amine or amine diluted with an aprotic or protic organic solvent, followed by an inorganic or organic acid.

19. The process of claim 18, wherein HCl is employed as an inorganic acid.

20. The process of claim 1, wherein the suspension obtained from carboxylic acid ester, alkali metal alkoxide and CO in an aprotic organic solvent is added to a suspension of the ammonium salt in an aprotic or protic organic solvent.

* * * * *

UNITED STATES PATENT AND TRADEMARK OFFICE
CERTIFICATE OF CORRECTION

PATENT NO. : 5,030,747

DATED : July 9, 1991

INVENTOR(S) : Blank et al.

It is certified that error appears in the above-identified patent and that said Letters Patent is hereby corrected as shown below:

Title Page      [54] Title: Delete "$\mu$-AMINO" and substitute -- $\beta$-AMINO --

Title Page      [75] Inventors: Delete "Halmut" and substitute -- Helmut --

Title page [56]    FOREIGN PATENT DOCUMENTS: Delete "569/" and substitute -- 560/ --

Title Page [57] ABSTRACT: Line 7 before "⊙" insert -- X --

Col. 1, line 2    Title: Delete "$\mu$-AMINO" and substitute -- $\beta$-AMINO --

Signed and Sealed this

Twenty-fifth Day of May, 1993

Attest:

MICHAEL K. KIRK

*Attesting Officer*      Acting Commissioner of Patents and Trademarks